(12) United States Patent
Moore et al.

(10) Patent No.: US 11,000,634 B2
(45) Date of Patent: May 11, 2021

(54) MEDICAL DEVICES USING COATED POLYMERS

(71) Applicants: AUSHEALTH CORPORATE PTY LTD, Underdale (AU); UNIVERSITY OF SOUTH AUSTRALIA, Adelaide (AU)

(72) Inventors: Eli Moore, Aberfoyle Park (AU); Glen Leon Benveniste, Ashford (AU); Claudine Sharon Bonder, Prospect (AU); Nicolas Hans Voelcker, Blackwood (AU)

(73) Assignees: AUSHEALTH CORPORATE PTY LTD, Underdale (AU); UNIVERSITY OF SOUTH AUSTRALIA, Adelaide (AU)

( * ) Notice: Subject to any disclaimer, the term of this patent is extended or adjusted under 35 U.S.C. 154(b) by 0 days.

(21) Appl. No.: 16/085,965

(22) PCT Filed: Mar. 17, 2017

(86) PCT No.: PCT/AU2017/050243
§ 371 (c)(1),
(2) Date: Sep. 17, 2018

(87) PCT Pub. No.: WO2017/156593
PCT Pub. Date: Sep. 21, 2017

(65) Prior Publication Data
US 2019/0099524 A1  Apr. 4, 2019

(30) Foreign Application Priority Data
Mar. 17, 2016 (AU) ................ 2016901009

(51) Int. Cl.
*A61L 31/10* (2006.01)
*C09D 171/08* (2006.01)
(Continued)

(52) U.S. Cl.
CPC .............. *A61L 31/10* (2013.01); *A61L 31/06* (2013.01); *A61L 33/0082* (2013.01);
(Continued)

(58) Field of Classification Search
None
See application file for complete search history.

(56) References Cited

U.S. PATENT DOCUMENTS 10,238,581 B2 * 3/2019 Deng .................. A61K 9/0014

FOREIGN PATENT DOCUMENTS

| WO | WO-2002/102864 A1 | 12/2002 |
| WO | WO-2008/074154 A1 | 6/2008 |

(Continued)

OTHER PUBLICATIONS

Boulares-Pender et al. (Functionalization of Plasma-Treated Polymer Surface with Glycidol, Journal of Applied Polymer Science, vol. 121, 2543-2550 (2011). (Year: 2011).*
(Continued)

*Primary Examiner* — Melissa S Mercier
(74) *Attorney, Agent, or Firm* — Fenwick & West LLP

(57) ABSTRACT

The present disclosure relates to medical devices using coated polymers, methods for reducing platelet attachment and/or fouling associated with medical devices, and methods for coating polymers. Certain embodiments of the present disclosure provide a medical device comprising one or more polymeric materials coated with a hyperbranched polyglycerol.

3 Claims, 2 Drawing Sheets

(51) Int. Cl.
  A61L 33/00    (2006.01)
  C09D 171/02   (2006.01)
  C08G 65/22    (2006.01)
  A61L 31/06    (2006.01)
(52) U.S. Cl.
  CPC .......... *A61L 33/0094* (2013.01); *C08G 65/22* (2013.01); *C09D 171/02* (2013.01); *C09D 171/08* (2013.01); *A61L 2400/18* (2013.01); *A61L 2420/02* (2013.01)

(56) References Cited

FOREIGN PATENT DOCUMENTS

| WO | WO-2013/130850 A1 | | 9/2013 | |
| WO | WO-2015-036364 A1 | | 3/2015 | |
| WO | WO-2015036364 A1 | * | 3/2015 | ........... C09D 5/1693 |

OTHER PUBLICATIONS

Deng et al. (The effect of Hyperbranches Polyglycerol Coating of Drug Delivery Using Degradable Polymer Nanoparticles, Biomaterials, May 9, 2014). (Year: 2014).*
PCT International Search Report & Written Opinion, International Application No. PCT/AU2017/050243, dated May 4, 2017, 14 Pages.
Boulares-Pender, a., et al., "Functionalization of Plasma-Treated Polymer Surfaces with Glycidol," Journal of Applied Polymer Science, 2011, pp. 2543-2550, vol. 121.
Fernandes, E.G.R., et al., "Antithrombogenic properties of bioconjugate streptokinase-polyglycerol dendrimers," Journal of Materials Science: Materials in Medicine, 2006, pp. 105-111, vol. 17.
Li, X., et al., "Negatively charged hyperbranched polyglycerol grafted membranes for osmotic power generation from municipal wastewater," Water Research, 2016, pp. 50-58, vol. 89.
Pranantyo, D., et al., "Antifouling Coatings via Tethering of Hyperbranched Polyglycerols on Biomimetic Anchors," Industrial & Engineering Chemistry Research, 2016, pp. 1890-1901, vol. 55.
Weber, T., et al., "Direct grafting of anti-fouling polyglycerol layers to steel and other technically relevant materials," Colloids and Surfaces B: Biointerfaces, 2013, pp. 360-366, vol. 111.
ASM International, *Materials and Processes for Medical Devices*, ASM International: The Materials Information Society, Nov. 2009.
Browne, M.M. et al., "Protein adsorption onto polystyrene surfaces studies by XPS and AFM," Science Direct, Elsevier, Surface Science, Jan. 27, 2004, vol. 553, pp. 155-167.
Khan, M. et al.,"Hyperbranched Polyglycidol on Si/SiO2 Surfaces via Surface-Initiated Polymerization," Macromolecules, 2003, vol. 36, No. 14, pp. 5088-5093.
Kucklick, T.R., "Introduction to Medical Plastics," *The Medical Device R&D Handbook*, Second Edition, CRC Press, Taylor & Francis Group, 2013, 48 pages.
Michelmore, A. et al., "On the effect of monomer chemistry on growth mechanisms of nonfouling PEG-like plasma polymers," Langmuir, 2013, vol. 29, No. 8, pp. 2595-2601.
Moore, E., et al., "Surface-Initiated Hyperbranched Polyglycerol as an Ultralow-Fouling Coating on Glass, Silicon, and Porous Silicon Substrates," ACS Applied Materials & Interfaces, 2014, vol. 6, No. 17, pp. 15243-15252.
Sunder, A., et al., "Controlled Synthesis of Hyperbranched Polyglycerols by Ring-Opening Multibranching Polymerization," Macromolecules, 1999. vol. 32, No. 13, pp. 4240-4246.
Teo, A.J.T et al., "Polymeric Biomaterials for Medical Implants and Devices," ACS Biomaterials Science & Engineering, 2016, vol. 2, pp. 454-472.
Utrata-Wesołek, A., et al., "Branched polyglicidol and its derivatives grafted-from polyethylene terephthalate) and silica as surfaces that reduce protein fouling," European Polymer Journal, 2018, vol. 105, p. 313-322.
Benson, A.M, et al., "Synthesis of a low thrombogenic heart valve coating with horseradish peroxidase," Polymers for Advanced Technologies, Jan. 7, 2005, pp. 117-122.

* cited by examiner

MEDICAL DEVICES USING COATED POLYMERS

PRIORITY CLAIM

This application claims priority to Australian provisional patent application number 2016901009 filed on 17 Mar. 2016, the content of which is hereby incorporated by reference.

FIELD

The present disclosure relates to medical devices using coated polymers, to methods for reducing platelet attachment and/or fouling associated with medical devices, and to methods for coating polymers.

BACKGROUND

Most medical devices implanted into a subject suffer from a loss of performance and/or longevity after implantation, in part due to interactions of the device with the tissue and/or fluids of the subject.

For example, synthetic vascular grafts are used in a variety of peripheral, aortic and vascular access procedures. However such devices often suffer a loss of performance or function over time from the effects of cell attachment, hyperplasia and thrombus formation associated with the grafts.

Similarly, stents are a commonly used medical device for the treatment of a number of conditions, such as their use in angioplasty to improve blood flow to narrowed or blocked coronary arteries, their use for peripheral artery angioplasty to treat atherosclerotic narrowing of the abdomen, leg and renal arteries caused by peripheral artery disease, and their use to assist in the treatment of aneurysms. However, not only do stents suffer a loss of function over time, but they also carry a risk of stent associated thrombosis due to clots forming in the stent.

The ability of medical devices such as grafts and stems to resist one or more of platelet attachment, cell attachment and fouling may have important effects on their usable lifespan and to reduce the possibility of adverse effects occurring in a patient.

Accordingly, there is a continuing need to provide medical devices with improved properties, and in particular, to provide devices which have one or more properties of reduced platelet attachment, reduced cell attachment and reduced fouling.

SUMMARY

The present disclosure relates to medical devices using coated polymers, to methods for reducing platelet attachment and/or fouling associated with medical devices, and to methods for coating polymers.

Certain embodiments of the present disclosure provide a medical device comprising one or more polymeric materials coated with a hyperbranched polyglycerol.

Certain embodiments of the present disclosure provide a polymeric medical device comprising one or more surfaces coated with a hyperbranched polyglycerol.

Certain embodiments of the present disclosure provide a graft comprising one or more polymeric materials coated with a hyperbranched polyglycerol.

Certain embodiments of the present disclosure provide a stent comprising one or more polymeric materials coated with a hyperbranched polyglycerol.

Certain embodiments of the present disclosure provide a method of reducing platelet attachment, fouling, cell attachment, anastomotic hyperplasia, clotting and/or thrombosis associated with a medical device comprising one or more polymeric materials, the method comprising coating the one or more polymeric materials with a hyperbranched polyglycerol.

Certain embodiments of the present disclosure provide a method of coating a polymeric substrate with a hyperbranched polyglycerol, the method comprising polymerisation of glycidol monomers to form a hyperbranched polyglycerol on the polymeric substrate and thereby coating the polymeric substrate with the hyperbranched polyglycerol.

Certain embodiments of the present disclosure provide a method of forming a hyperbranched polyglycerol coating on a polymeric substrate, the method comprising exposing the polymeric substrate to polymerisation of glycidol monomers and thereby forming a hyperbranched polyglycerol coating on the polymeric substrate.

Certain embodiments of the present disclosure provide a method of producing a medical device with one or more of reduced platelet attachment, fouling, reduced cell attachment, reduced inflammatory cell attachment, reduced anastomotic hyperplasia, reduced clotting and/or reduced thrombosis, the method comprising using a hyperbranched polyglycerol coated polymeric material in the device to reduce fouling, cell attachment, inflammatory cell attachment, anastomotic hyperplasia, clotting and/or thrombosis associated with the medical device.

Certain embodiments of the present disclosure provide a method of producing a polymeric medical device with one or more of reduced platelet attachment, reduced fouling, reduced cell attachment, reduced inflammatory cell attachment, reduced anastomotic hyperplasia, reduced clotting and/or reduced thrombosis, the method comprising coating the polymeric material in the medical device with a hyperbranched polyglycerol.

Other embodiments are described herein.

BRIEF DESCRIPTION OF THE FIGURES

Certain embodiments are illustrated by the following figures. It is to be understood that the following description is for the purpose of describing particular embodiments only and is not intended to be limiting with respect to the description.

DETAILED DESCRIPTION

Figure 1:
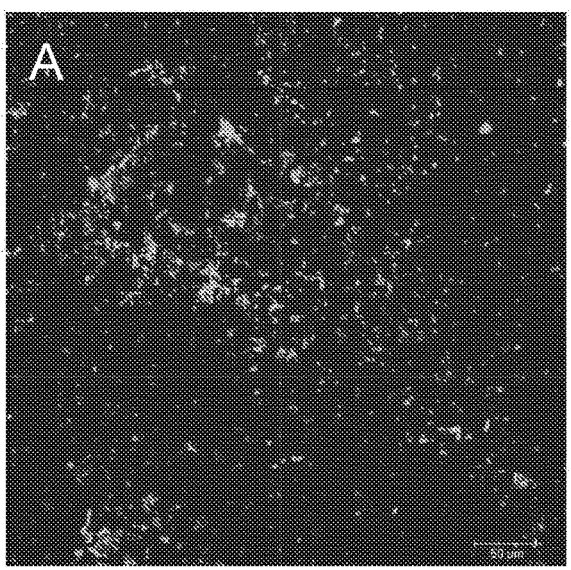
FIG. 1 shows attached platelets on bare ePTFE graft material (panel A) and on HPG-grafted ePTFE graft material (panel B), following incubation in platelet rich plasma for 2 hours at 37° C. Samples were washed lightly with PBS and remaining cells fixed with 4% paraformaldehyde and stained with carboxyfluorescein succinimidyl ester (CFSE).
Figure 1:
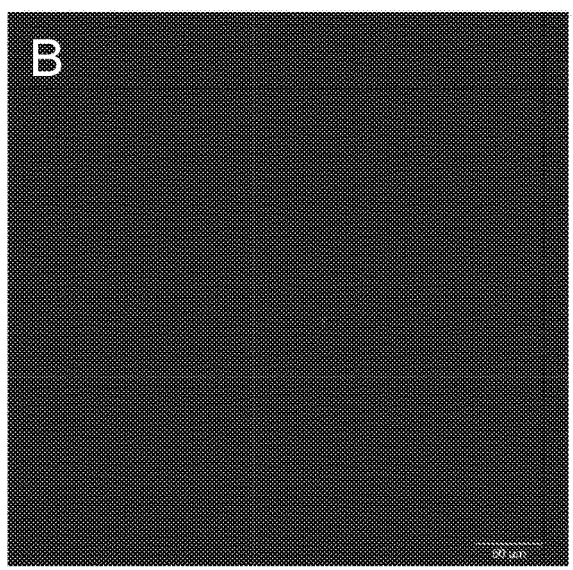

The present disclosure relates to medical devices using coated polymers, to methods for reducing platelet attachment and/or fouling associated with medical devices, and to methods for coating polymers.

Certain embodiments of the present disclosure provide a medical device comprising one or more polymeric materials coated with a hyperbranched polyglycerol The term "polymeric material", and related terms such as "polymeric substrate", as used herein refers to a material that comprises one or more chemical compounds made up of a plurality of repeating similar structural units. Examples of polymeric materials include synthetic materials made of organic polymers (such as plastics and resins), and natural materials such as silk, wool, cellulose rubber and biological macromolecules.

Methods for producing polymeric materials are known in the art. Methods for using polymeric materials in medical devices are known in the art, for example as described in Teo et at. (2016) *ACS Biomater. Sci. Eng.* 2(4): 454-472. Methods for manufacturing medical devices incorporating, and/or coated with, one or more polymeric materials are known in the art, for example as described in "The Medical Device R&D Handbook" (2013) edited by T. E. Kuclick CRC Press, In certain embodiments, the one or more polymeric material comprises a thermoplastic, an elastomer, a thermoset or a fibre.

In certain embodiments, the one or more polymeric materials comprise one or more of a fluoropolymer, a polyester and/or a polyurethane.

In certain embodiments, the one or more polymeric materials comprise one or more fluoropolymers. Methods for synthesis of fluoropolymers are known in the art.

Examples of fluoropolymers comprise one or more a PVF (polyvinylfluoride), a PVDF (polyvinylidene fluoride), a PTFE (polytetrafluoroethylene), a PCTFE (polychlorotrifluoroethylene), a PFA/MFA (perfluoroalkoxy polymer), a FEP (fluorinated ethylene-propylene), an ETFE (polyethylenetetrafluoroethyllene), an ECTFE (polyethylenechlorotrifluoroethylene), a FFPM/FFKM (perfluorinated elastomer), a FPM/FKM (fluorocarbon [chlorotrifluoroethylenevinylidene fluoride]), a FEPM (tetrafluoroethylene-propylene), a PFPE (perfluoropolyether), and a PFSA (perfluorosulfonic acid) and a perfluoropolyoxetane. Other fluoropolymers are contemplated.

Methods for producing medical devices incorporating fluoropolymers, and/or coating medical devices with fluoropolymers, are known in the art, for example as described in "Materials and Coatings for Medical Devices: Cardiovascular" (2009) ASM International, ISBN: 978-1-61503-000-2.

In certain embodiments, the one or more polymeric materials comprise a polytetrafluoroethylene polymer and/or a substituted derivative thereof.

In certain embodiments, the one or more polymeric materials comprise one or more polyesters. Methods for synthesis of polyesters are known in the art. Methods for producing medical devices incorporating polyesters, and/or coating medical devices with polyesters, are known in the art, for example as described in "Materials and Coatings for Medical Devices: Cardiovascular" (2009) ASM International, ISBN: 978-1-61503-000-2.

Examples of polyesters comprise one or more of a polyglycolide or polyglycolic acid (PGA), a polylactic acid (PLA), a polycaprolactone (PCL), a polyhydroxyalkanoate (PHA), a polyhydroxybutyrate (PHB), a polyethylene adipate (PEA), a polybutylene succinate (PBS), a poly(3-hydroxybutyrate-co-3-hydroxyvalerate) (PHBV), a polyethylene terephthalate (PET), a polybutylene terephthalate (PBT), a polytrimethylene terephthalate (PTT), a polyethylene naphthalate (PEN), and Vectran. Other polyesters are contemplated.

In certain embodiments, the one or more polymeric materials comprise a polyethylene terephthalate and/or a substituted derivative thereof.

In certain embodiments, the one or more polymeric materials comprise one or more polyurethanes. Methods for producing medical devices incorporating polyurethanes, and/or coating medical devices with polyurethanes, are known in the art, for example as described in "Materials and Coatings for Medical Devices: Cardiovascular" (2009) ASM International, ISBN: 978-1-61503-000-2.

Examples of polyurethanes include one or more of thermoplastic polyurethane, thermoplastic polycarbonate-urethane (PCU), segmented polyurethane (SPU), thermoplastic silicone-polycarbonate-urethane (TSPCU), thermoplastic polyether-urethane (TPU), and thermoplastic Silicone-Polyether-urethane (TSPU). Other polyurethanes are contemplated.

In certain embodiments, the one or more polymeric materials comprise one or more thermoplastic polyurethanes.

In certain embodiments, the medical device comprises a graft, a stent, a cannula, a catheter, a guide wire, a patch, a sheath, a suture, or a valve. Other types of medical devices are contemplated. Methods for manufacturing medical devices from, or incorporating, polymeric materials are known in the art.

In certain embodiments, the medical device comprises a medical device for use in a vascular setting. In certain embodiments, the medical device comprises a vascular graft, a vascular stent or a vascular cannula.

In certain embodiments, the medical device is an arterial graft or a venous graft. Methods for manufacturing grafts incorporating, and/or coated with, polymeric materials are known in the art. For example, the medical device may be a graft made from a PTFE (eg commercially available from Gore Devices—GORE-TEX Vascular Grafts), a polyester (eg a Dacron graft, commercially available from Terumo) or a polyurethane.

In certain embodiments, the medical device is a stent. In certain embodiments, the medical device is a vascular stent, such as a coronary stent.

In certain embodiments, the medical device comprises a medical device for use in a non-vascular setting.

The term "hyperbranched polyglycerol" as used herein refers to a branched aliphatic polyether with hydroxyl end groups. It will be appreciated that the term also includes a branched polyether in which a proportion of the hydroxyl end groups have been derivatised and/or replaced with a suitable group.

In certain embodiments, the medical device comprises one or more other coatings, or a coating comprising a hyperbranched polyglycerol and one or more other materials, such as another polymer.

In certain embodiments, the hyperbranched polyglycerol coating comprises a thickness of 5 nm or more, 6 nm or more, 7 nm or more, 8 nm or more, 9 nm or more, 10 nm or more, 20 nm or more, 50 nm or more or 100 nm or more.

In certain embodiments, the hyperbranched polyglycerol coating comprises a thickness of at least 5 nm, at least 6 nm, at least 7 nm, at least 8 nm, at least 9 nm, at least 10 nm, at least 20 nm, at least 50 nm or at least 100 nm. A suitable thickness relevant to the application of the device may be selected. Methods for determining the thickness of a coating are known in the art.

In certain embodiments, the coating is formed by a reaction comprising polymerisation of glycidol monomers (directly or indirectly) on the one or more polymeric materials. In certain embodiments, the medical device comprises a coating formed by a reaction comprising polymerisation of glycidol monomers on the one or more polymeric materials. In certain embodiments, the one or more polymeric materials coated with a hyperbranched polyglycerol comprise a coating formed by a reaction comprising polymerisation of glycidol monomers on the one or more polymeric materials.

In certain embodiments, the polymerisation of the glycidol monomers comprises a ring opening reaction of the glycidol monomers. Other synthetic methods are contemplated.

In certain embodiments, the coating is formed by a reaction comprising a single (non-iterative) reaction synthesis of monomers. In certain embodiments, the coating is formed by reactions comprising multiple (iterative) reaction syntheses of monomers.

In certain embodiments, the coating is formed directly on the polymeric material.

In certain embodiments, the coating is formed directly on activated polymeric material. In certain embodiments, the coating is formed directly on plasma activated polymeric material. In certain embodiments, the polymeric material is activated by plasma treatment and the coating is formed on the activated material.

In certain embodiments, the coating is formed indirectly on the polymeric material.

In certain embodiments, the coating is formed on functionalised polymeric material. In certain embodiments, the polymeric material is functionalised and the coating is formed on the functionalised polymeric material.

Methods for functionalisation of surfaces/substrates are known in the art. Methods for formation of polymers or other materials on a functionalised surface/substrate are known in the art. For example, polyurethane may be functionalised by treatment with a diisocyanate to introduce free isocyanate groups for coupling.

Other methods of forming a coating on the polymeric material are contemplated, such as deposition of a plasma polymer containing amines and which may initiate ring opening polymerisation of glycidol.

In certain embodiments, the coating is formed on the one or more polymeric materials by a method comprising one or more of activation by plasma treatment, plasma polymerisation, covalent bonding directly to the one or more polymeric materials, or covalent bonding indirectly to the one or more polymeric materials. In certain embodiments, the coating is formed from a method involving chemical activation of the polymeric material. Other methods are contemplated.

For example, plasma polymerisation may be performed as described in Michelmore et al. (2013) *Langmuir* 29(8): 2595-2601.

Chemical methods for activating a polymeric material to allow formation of a coating (directly or indirectly) on the material are also known in the art.

In certain embodiments, the coating is formed on the one or more polymeric materials activated by plasma treatment.

In certain embodiments, the polymeric material is activated by plasma treatment and the coating is formed (directly or indirectly) on the activated material.

Examples of plasma treatment include radio frequency induced plasma treatment, corona plasma treatment, glow discharge plasma treatment, plasma immersion ion implantation, low pressure plasma treatment, and atmospheric pressure plasma treatment. Methods for plasma treatment of materials or substrates to form plasma modified/activated surfaces are known in the art.

In certain embodiments, the coating is formed on the one or more polymeric materials activated by plasma treatment in the presence of a gas. Examples of gases comprise one of more of oxygen, argon, nitrous oxide, tetrafluoromethane, and air.

In certain embodiments, the coating is formed on one or more polymeric material activated by plasma treatment in the presence of one or more non-depositing gases. In certain embodiments, the non-depositing gas comprises argon or another noble gas such as helium or neon.

In certain embodiments, the plasma treatment comprises radio frequency induced plasma treatment. Other types of plasma treatment are contemplated.

In certain embodiments, the plasma treatment comprises treatment using a power in the range of 10 W or greater, 20 W or greater, 50 W or greater or 100 W or greater. In certain embodiments, the plasma treatment comprises treatment using a power in the range of 10 W or greater. Other ranges are contemplated.

In certain embodiments, the plasma treatment comprises treatment using a power in the range of 10 W to 500 W, 10 to 100 W, 20 to 500 W, 20 to 100 W, 50 to 500 W, 50 to 100 W, or 100 to 500 W. In certain embodiments, the plasma treatment comprises treatment using a power in the range of 100 W to 500 W. Other ranges are contemplated.

In certain embodiments, the plasma treatment comprises a pressure of $1.0 \times 10^{-3}$ bar or more, $5.0 \times 10^{-3}$ bar or more, $8.0 \times 10^{-3}$ bar or more, $1 \times 10^{-2}$ bar or more, $2.0 \times 10^{-2}$ bar or more, or $5.0 \times 10^{-2}$ bar. Other pressures are contemplated.

In certain embodiments, the plasma treatment comprises use of a pressure of $1.0 \times 10^{-3}$ bar or less, $5.0 \times 10^{-3}$ bar or less, $8.0 \times 10^{-3}$ bar or less, $1 \times 10^{-2}$ bar or less, $2.0 \times 10^{-2}$ bar or less, or $5.0 \times 10^{-2}$ bar or less.

In certain embodiments, the method comprises activating the polymeric material by plasma treatment and forming the hyperbranched polyglycerol coating by contacting the activated material with glycidol monomers to initiate polymerisation of the monomers.

In certain embodiments, the hyperbranched polyglycerol coating is formed by a reaction that comprises exposing the polymeric material to glycidol monomers substantially in the absence of glycidol in a solvent. In certain embodiments, the hyperbranched polyglycerol coating is formed by exposing the polymeric material to substantially undiluted glycidol monomers. In certain embodiments, the hyperbranched polyglycerol coating is formed by exposing the polymeric material to substantially pure glycidol. In certain embodiments, the hyperbranched polyglycerol coating is formed by exposing the polymeric material to glycidol substantially free of a solvent. In certain embodiments, the hyperbranched polyglycerol coating is formed by a reaction that does not comprise exposing the polymeric material to glycidol monomers in a solvent. The term "solvent" as used herein refers to a substance that dissolves glycidol, and may or may not be chemically inert.

In certain embodiments, the hyperbranched polyglycerol coating is formed by exposing the polymeric material to a solution comprising at least 90% glycidol, at least 95% glycidol, at least 96% glycidol, at least 97% glycidol, at least 98% glycidol, or at least 99% glycidol.

In certain embodiments, the polymerisation of glycidol monomers comprises polymerisation using a solution comprising at least 90% glycidol, at least 95% glycidol, at least 96% glycidol, at least 97% glycidol, at least 98% glycidol, or at least 99% glycidol. In certain embodiments, the polymerisation of glycidol monomers comprises using a solution comprising at least 96% glycidol.

In certain embodiments, the one or more polymeric materials in the medical device are coated prior to production of the medical device. For example, a medical device may be produced from polymeric materials that have been pre-coated with a hyperbranched polyglycerol.

In certain embodiments, the one or more polymeric materials in the medical device are coated after production of the medical device. For example, a medical device may be produced and the polymeric materials in the device subsequently coated with a hyperbranched polyglycerol. For example, a medical device may be plasma treated and the coating formed on the device by treating with glycidol monomers.

In certain embodiments, the medical device comprises one or more polymeric surfaces coated with a hyper-branched polyglycerol.

Certain embodiments of the present disclosure provide a polymeric medical device comprising one or more surfaces coated with a hyperbranched polyglycerol.

Certain embodiments of the present disclosure provide a graft comprising one or polymeric materials coated with a hyperbranched polyglycerol.

In certain embodiments, the graft is a vascular graft.

Certain embodiments of the present disclosure provide a vascular graft comprising a polytetrafluoroethylene (PTFE) coated with a hyperbranched polyglycerol.

Certain embodiments of the present disclosure provide a polytetrafluoroethylene (PTFE) vascular graft comprising a hyperbranched polyglycerol coating.

Certain embodiments of the present disclosure provide a vascular graft comprising a polyester coated with a hyper-branched polyglycerol.

Certain embodiments of the present disclosure provide a polyester vascular graft comprising a hyperbranched polyglycerol coating.

Certain embodiments of the present disclosure provide a vascular graft comprising a polyurethane coated with a hyperbranched polyglycerol.

Certain embodiments of the present disclosure provide a polyurethane vascular graft comprising a hyperbranched polyglycerol coating.

Certain embodiments of the present disclosure provide a stent comprising one or more polymeric materials coated with a hyperbranched polyglycerol.

In certain embodiments, the stent is a vascular stent.

Medical devices and polymeric materials are as described herein. Methods for coating polymeric surfaces with a hyperbranched polyglycerol are as described herein.

In certain embodiments, a medical device as described herein comprises one or more characteristics in use selected from reduced attachment of platelets to the coated polymeric material, reduced attachment of cells (such as inflammatory cells) and/or proteins to the coated polymeric material, reduced fouling, reduced clotting, reduced thrombosis and reduced anastomotic hyperplasia.

In certain embodiments, the reduction of one or more of the aforementioned characteristics comprises a reduction by at least 10%, at least 20%, at least 30%, at least 40%, at least 50%, at least 60%, at least 70%, at least 80%, or at least 90%, as compared to uncoated polymeric material.

In certain embodiments, the attachment of platelets and/or the attachment of cells is reduced by at least 10%, at least 20%, at least 30%, at least 40%, at least 50%, at least 60%, at least 70%, at least 80%, or at least 90%, as compared to uncoated polymeric material.

Certain embodiments of the present disclosure provide a medical device as described herein with one or more of reduced fouling, reduced attachment of platelets or cells, reduced clotting, reduced thrombosis and reduced anastomotic hyperplasia.

Certain embodiments of the present disclosure provide use of a medical device as described herein. For example, a medical device as described herein may be used to treat a vascular condition.

Certain embodiments of the present disclosure provide use of a medical device as described herein to prevent and/or treat a condition selected from arterial or venous narrowing, ischemia, angina, an aneurysm, or to repair or support an artery or vein. Other diseases, conditions or states are contemplated.

Certain embodiments of the present disclosure provide a method of treating a condition in a subject that would benefit from the introduction of a medical device as described herein, such as vascular graft or a stent. In certain embodiments, the condition is a vascular condition. In certain embodiments, the vascular condition comprises arterial or venous narrowing, angina, an aneurysm, or repair or support of an artery or vein.

Certain embodiments of the present disclosure provide a method of reducing platelet attachment, fouling, cell attachment, anastomotic hyperplasia, clotting and/or thrombosis associated with a medical device comprising one or more polymeric materials, the method comprising coating the one or more polymeric materials with a hyperbranched polyglycerol.

Medical devices are described herein. In certain embodiments, the medical device comprises a graft, a stent or a cannula. In certain embodiments, the medical device comprises a vascular graft, a vascular stent or a vascular cannula.

Polymeric materials, and methods for coating polymeric materials, substrates or surfaces with a hyperbranched polyglycerol, are as described herein.

In certain embodiments, the one or more polymeric materials comprise a fluoropolymer, a polyester and/or a polyurethane.

In certain embodiments, the fluoropolymer comprises a polytetrafluoroethylene polymer.

Methods for forming hyperbranched polyglycerol are described herein.

In certain embodiments, the coating comprises formation of the coating directly on the one or more polymeric materials. In certain embodiments, the coating comprises formation of the coating indirectly on the one or more polymeric materials.

In certain embodiments, the coating of the one or more polymeric materials comprises polymerisation of glycidol monomers on the one or more polymeric materials.

In certain embodiments, the polymerisation of the glycidol monomers comprises a ring opening reaction of the glycidol monomers.

In certain embodiments the coating comprises activation of the one or more polymeric materials.

In certain embodiments the coating comprises activation of the one or more polymeric materials by plasma treatment. Methods for performing plasma treatment are as described herein.

In certain embodiments, the coating comprises activation of the one or more polymeric materials by plasma treatment in the presence of one or more of oxygen, argon, nitrous oxide, tetrafluoromethane and air.

In certain embodiments, the coating is formed on the one or more polymeric materials activated by plasma treatment in the presence of one or more non-depositing gases. In certain embodiments, the non-depositing gas comprises argon.

In certain embodiments, the plasma treatment comprises radio frequency induced plasma treatment.

In certain embodiments, the coating comprises forming a coating with a thickness of 5 nm or more, 6 nm or more, 7 nm or more, 8 nm or more, 9 nm or more, 10 nm or more, 20 nm or more, 50 nm or more or 100 nm or more.

In certain embodiments, the coating comprises forming a coating with a thickness of at least 5 nm, at least 6 nm, at least 7 nm, at least 8 nm, at least 9 nm, at least 10 nm, at least 20 nm, at least 50 nm or at least 100 nm. A suitable thickness relevant to the application of the device may be selected. Methods for determining the thickness of a coating are known in the art.

In certain embodiments, the coating exposing the polymeric material to glycidol monomers substantially in the absence of a solvent. In certain embodiments, the coating comprises exposing the polymeric material to substantially undiluted glycidol monomers. In certain embodiments, the coating comprises exposing the polymeric material to substantially pure glycidol. In certain embodiments, the coating comprises exposing the polymeric material to glycidol substantially free of a solvent. In certain embodiments, the coating comprises exposing the polymeric material to glycidol monomers not in a solvent.

In certain embodiments, the coating comprises exposing the polymeric material to a solution comprising at least 90% glycidol, at least 95% glycidol, at least 96% glycidol, at least 97% glycidol, at least 98% glycidol, or at least 99% glycidol.

In certain embodiments, the polymerisation of glycidol monomers comprises polymerisation using a solution comprising at least 90% glycidol, at least 95% glycidol, at least 96% glycidol, at least 97% glycidol, at least 98% glycidol, or at least 99% glycidol.

Certain embodiments of the present disclosure provide a method of coating a polymeric substrate with a hyperbranched polyglycerol, the method comprising polymerisation of glycidol monomers to form a hyperbranched polyglycerol on the polymeric substrate and thereby coating the polymeric substrate with the hyperbranched polyglycerol.

Polymeric substrates, and methods for coating polymeric substrates with a hyperbranched polyglycerol, are as described herein.

In certain embodiments, the polymeric substrate comprises a thermoplastic, an elastomer, a thermoset or a fibre.

In certain embodiments, the polymeric substrate comprises a fluoropolymer, a polyester and/or a polyurethane.

In certain embodiments, polymeric substrate comprises one or more fluoropolymers. Methods for synthesis of fluoropolymers are known in the art.

Examples of fluoropolymers comprise one or more a PVF (polyvinylfluoride), a PVDF (polyvinylidene fluoride), a PTFE (polytetrafluoroethylene), a PCTFE (polychlorotrifluoroethylene), a PFA/MFA (perfluoroalkoxy polymer), a FEP (fluorinated ethylene-propylene), an ETFE (polyethylenetetrafluoroethylene), an ECTFE (polyethylenechlorotrifluoroethylene FFPM/FFKM (perfluorinated elastomer), a FPM/FKM (fluorocarbon [chlorotrifluoroethylenevinylidene fluoride]), a FEPM (tetrafluoroethylene-propylene), a PFPE (perfluoropolyether), and a PFSA (perfluorosulfonic acid) and a perfluoropolyoxetane. Other fluoropolymers are contemplated.

In certain embodiments, the polymeric substrate comprises polytetrafluoroethylene polymer and/or a substituted derivative thereof.

In certain embodiments, the polymeric substrate comprises one or more polyesters. Methods for synthesis of polyesters are known in the art.

Examples of polyesters comprises one or more of a polyglycolide or polyglycolic acid (PGA), a polylactic acid (PLA), a polycaprolactone (PCL), a polyhydroxyalkanoate (PHA), a polyhydroxybutyrate (PHB), a polyethylene adipate (PEA), a polybutylene succinate (PBS), a poly(3-hydroxybutyrate-co-3-hydroxyvalerate) (PHBV), a polyethylene terephthalate (PET), a polybutylene terephthalate (PBT), a polytrimethylene terephthalate (PTT), a polyethylene naphthalate (PEN), and Vectran. Other polyesters are contemplated.

In certain embodiments, the polymeric substrate comprises a polyethylene terephthalate and/or a substituted derivative thereof.

In certain embodiments, the polymeric substrate comprises one or more polyurethanes. Methods for producing polyurethanes are known in the art.

Examples of polyurethanes include one or more of thermoplastic polyurethane, thermoplastic polycarbonate-urethane (PCU), segmented polyurethane (SPU), thermoplastic silicone-polycarbonate-urethane (TSPCU), thermoplastic polyether-urethane (TPU), and thermoplastic Silicone-Polyether-urethane (TSPU). Other polyurethanes are contemplated.

In certain embodiments, the polymeric substrate comprises one or more thermoplastic polyurethanes.

Methods for forming hyperbranched polyglycerol are as described herein.

In certain embodiments, the method comprises formation of the coating directly on the polymeric substrate. In certain embodiments, the method comprises formation of the coating directly on activated polymeric substrate. In certain embodiments, the method comprises formation of the coating directly on plasma activated polymeric substrate.

In certain embodiments, the coating of the one or more polymeric substrate comprises polymerisation of glycidol monomers on the polymeric substrate.

In certain embodiments, the polymerisation of the glycidol monomers comprises a ring opening reaction of the glycidol monomers.

In certain embodiments the coating comprises activation of the polymeric substrate by plasma treatment. Examples of plasma treatments, and methods for performing plasma treatment, are as described herein.

In certain embodiments, the method comprises activation of the polymeric substrate by plasma treatment in the presence of one or more of one or more of oxygen, argon, nitrous oxide, tetrafluoromethane and air.

In certain embodiments, the method comprises activation by plasma treatment in the presence of one or more non-depositing gases.

In certain embodiments, the plasma treatment comprises radio frequency induced plasma treatment.

In certain embodiments, the method comprises exposing the substrate to glycidol monomers substantially in the absence of a solvent. In certain embodiments, the method comprises exposing the substrate to substantially undiluted glycidol monomers. In certain embodiments, the method comprises exposing the substrate to substantially pure glycidol. In certain embodiments, the method comprises exposing the substrate to glycidol substantially free of a solvent. In certain embodiments, the coating comprises exposing the polymeric material to glycidol monomers not in a solvent. In certain embodiments, the method does not comprise exposing the substrate to the glycidol monomers in the presence of a solvent.

In certain embodiments, the method comprises exposing the substrate to a solution comprising at least 90% glycidol, at least 95% glycidol, at least 96% glycidol, at least 97% glycidol, at least 98% glycidol, or at least 99% glycidol.

In certain embodiments, the polymerisation of glycidol monomers comprises polymerisation using a solution comprising at least 90% glycidol, at least 95% glycidol, at least 96% glycidol, at least 97% glycidol, at least 98% glycidol, or at least 99% glycidol.

In certain embodiments, the plasma treatment comprises treatment using a power in the range of 10 W or greater, 20 W or greater, 50 W or greater or 100 W or greater. In certain embodiments, the plasma treatment comprises treatment using a power in the range of 10 W or greater. Other ranges are contemplated.

In certain embodiments, the plasma treatment comprises treatment using a power in the range of 10 W to 500 W, 10 to 100 W, 20 to 500 W, 20 to 100 W, 50 to 500 W, 50 to 100 W, or 100 to 500 W. In certain embodiments, the plasma treatment comprises treatment using a power in the range of 100 W to 500 W. Other ranges are contemplated.

In certain embodiments, the plasma treatment comprises a pressure of $1.0 \times 10^{-3}$ bar or more, $5.0 \times 10^{-3}$ bar or more, $8.0 \times 10^{-3}$ bar or more, $1 \times 10^{-2}$ bar or more, $2.0 \times 10^{-2}$ bar or more, or $5.0 \times 10^{-2}$ bar or more. Other pressures are contemplated.

In certain embodiments, the plasma treatment comprises use of a pressure of $1.0 \times 10^{-3}$ bar or less, $5.0 \times 10^{-3}$ bar or less, $8.0 \times 10^{-3}$ bar or less, $1 \times 10^{-2}$ bar or less, $2.0 \times 10^{-2}$ bar or less, or $5.0 \times 10^{-2}$ bar or less.

In certain embodiments, the method comprises activating the polymeric substrate by plasma treatment and contacting the activated substrate with the glycidol monomers to initiate polymerisation of the monomers.

In certain embodiments, the method comprises forming a coating with a thickness of 5 nm or more, 6 nm or more, 7 nm or more, 8 nm or more, 9 nm or more, 10 nm or more, 20 nm or more, 50 nm or more or 100 nm or more.

In certain embodiments, the method comprises forming a coating with a thickness of at least 5 nm, at least 6 nm, at least 7 nm, at least 8 nm, at least 9 nm, at least 10 nm, at least 20 nm, at least 50 nm or at least 100 nm. A suitable thickness relevant to the application of the device may be selected. Methods for determining the thickness of a coating are known in the art.

In certain embodiments, the coating of the polymeric substrate results in the substrate having one or more characteristics in use selected from reduced attachment of platelets to the coated substrate, reduced attachment of cells and/or proteins to the coated substrate, reduced fouling, reduced clotting, reduced thrombosis and reduced anastomotic hyperplasia.

In certain embodiments, the reduction of one or more of the aforementioned characteristics comprises a reduction by at least 10%, at least 20%, at least 30%, at least 40%, at least 50%, at least 60%, at least 70%, at least 80%, or at least 90%, as compared to an uncoated substrate.

In certain embodiments, the attachment of platelets and/or the attachment of cells is reduced by at leak 10%, at least 20%, at least 30%, at least 40%, at least 50%, at least 60%, at least 70%, at least 80%, or at least 90%, as compared to an uncoated substrate.

In certain embodiments, the methods as described herein are used to coat one or more surfaces of a medical device.

Certain embodiments of the present disclosure provide a polymeric substrate coated by method as described herein.

Certain embodiments of the present disclosure provide a medical device comprising a coated polymeric substrate as described herein.

Certain embodiments of the present disclosure provide a polymeric medical device comprising one or more surfaces coated with a hyperbranched polyglycerol.

Certain embodiments of the present disclosure provide a medical device with one or more of reduced platelet attachment, reduced cell attachment, reduced fouling, reduced clotting, reduced thrombosis and reduced anastomotic hyperplasia produced by coating the device by a method as described herein.

Certain embodiments of the present disclosure provide a method of forming a hyperbranched polyglycerol coating on a polymeric substrate, the method comprising exposing the polymeric substrate to polymerisation of glycidol monomers and thereby forming a hyperbranched polyglycerol coating on the polymeric substrate.

Polymeric substrates, and methods for exposing a polymeric substrate to coat the substrate with a hyperbranched polyglycerol using glycidol monomers, are as described herein.

In certain embodiments, the polymeric substrate comprises a thermoplastic, an elastomer, a thermoset or a fibre.

In certain embodiments, the polymeric substrate comprises a fluoropolymer, a polyester and/or a polyurethane.

In certain embodiments, polymeric substrate comprises one or more fluoropolymers. Methods for synthesis of fluoropolymers are known in the art.

Examples of fluoropolymers comprise one or more a PVF (polyvinylfluoride), a PVDF (polyvinylidene fluoride), a PTFE (polytetrafluoroethylene), a PCTFE (polychlorotrifluoroethylene), a PFA/MFA (perfluoroalkoxy polymer), a FEP (fluorinated ethylene-propylene), an ETFE (polyethylenetetrafluoroethylene), an ECTFE (polyethylenechlorotrifluoroethylene), a FFPM/FFKM (perfluorinated elastomer), a FPM/FKM (fluorocarbon [chlorotrifluoroethylenevinylidene fluoride]), a FEPM (tetrafluoroethylene-propylene), a PFPE (perfluoropolyether), and a PFSA (perfluorosulfonic acid) and a perfluoropolyoxetane. Other fluoropolymers are contemplated.

In certain embodiments, the polymeric substrate comprises a polytetrafluoroethylene polymer and/or a substituted derivative thereof.

In certain embodiments, the polymeric substrate comprises one or more polyesters. Methods for synthesis of polyesters are known in the art.

Examples of polyesters comprises one or more of a polyglycolide or polyglycolic acid (PGA), a polylactic acid (PLA), a polycaprolactone (PCL), a polyhydroxyalkanoate (PHA), a polyhydroxybutyrate (PHB), a polyethylene adipate (PEA), a polybutylene succinate (PBS), a poly(3-hydroxybutyrate-co-3-hydroxyvalerate) (PHBV), a polyethylene terephthalate (PET), a polybutylene terephthalate (PBT), a polytrimethylene terephthalate (PTT), a polyethylene naphthalate (PEN), and Vectran. Other polyesters are contemplated.

In certain embodiments, the polymeric substrate comprises a polyethylene terephthalate and/or a substituted derivative thereof.

In certain embodiments, the polymeric substrate comprises one or more polyurethanes. Methods for producing polyurethanes are known in the art.

Examples of polyurethanes include one or more of thermoplastic polyurethane, thermoplastic polycarbonate-urethane (PCU), segmented polyurethane (SPU), thermoplastic silicone-polycarbonate-urethane (TSPCU), thermoplastic polyether-urethane (TPU), and thermoplastic Silicone-Polyether-urethane (TSPU). Other polyurethanes are contemplated.

In certain embodiments, the polymeric substrate comprises one or more thermoplastic polyurethanes.

In certain embodiments, the polymerisation of the glycidol monomers comprises a ring opening reaction of the glycidol monomers.

In certain embodiments, the coating comprises activation of the polymeric substrate by plasma treatment. In certain embodiments the coating comprises activation of the polymeric substrate by plasma treatment. Methods for performing plasma treatment are as described herein.

In certain embodiments, the method comprises activation of the polymeric substrate by plasma treatment in the presence of one or more of one or more of oxygen, argon, nitrous oxide, tetrafluoromethane and air.

In certain embodiments, the method comprises activation of the polymeric substrate by plasma treatment in the presence of one or more non-depositing gases. In certain embodiments, the non-depositing gas comprises argon.

In certain embodiments, the plasma treatment comprises radio frequency induced plasma treatment.

In certain embodiments, the method comprises formation of the coating directly on the polymeric substrate.

In certain embodiments, the method comprises exposing the substrate to glycidol monomers substantially in the absence of a solvent. In certain embodiments, the method comprises exposing the substrate to substantially undiluted glycidol monomers. In certain embodiments, the method comprises exposing the substrate to substantially pure glycidol. In certain embodiments, the method comprises exposing the substrate to glycidol substantially free of a solvent. In certain embodiments, the coating comprises exposing the polymeric material to glycidol monomers not in a solvent. In certain embodiments, the method does not comprise exposing the substrate to the glycidol monomers in the presence of a solvent.

In certain embodiments, the method comprises exposing the substrate to a solution comprising at least 90% glycidol, at least 95% glycidol, at least 96% glycidol, at least 97% glycidol, at least 98% glycidol, or at least 99% glycidol.

In certain embodiments, the polymerisation of glycidol monomers comprises polymerisation using a solution comprising at least 90% glycidol, at least 95% glycidol, at least 96% glycidol, at least 97% glycidol, at least 98% glycidol, or at least 99% glycidol.

In certain embodiments, the plasma treatment comprises treatment using a power in the range of 10 W or greater, 20 W or greater, 50 W or greater or 100 W or greater. In certain embodiments, the plasma treatment comprises treatment using a power in the range of 10 W or greater. Other ranges are contemplated.

In certain embodiments, the plasma treatment comprises treatment using a power in the range of 10 W to 500 W, 10 to 100 W, 20 to 500 W, 20 to 100 W, 50 to 500 W, 50 to 100 W, or 100 to 500 W. In certain embodiments, the plasma treatment comprises treatment using a power in the range of 100 W to 500 W. Other ranges are contemplated.

In certain embodiments, the plasma treatment comprises a pressure of $1.0 \times 10^{-3}$ bar or more, $5.0 \times 10^{-3}$ bar or more, $8.0 \times 10^{-3}$ bar or more, $1 \times 10^{-2}$ bar or more, $2.0 \times 10^{-2}$ bar or more, or $5.0 \times 10^{-2}$ bar. Other pressures are contemplated.

In certain embodiments, the plasma treatment comprises use of a pressure of $1.0 \times 10^{-3}$ bar or less, $5.0 \times 10^{-3}$ bar or less, $8.0 \times 10^{-3}$ bar or less, $1 \times 10^{-2}$ bar or less, $2.0 \times 10^{-2}$ bar or less, or $5.0 \times 10^{-2}$ bar or less.

In certain embodiments, the method comprises activating the polymeric substrate by plasma treatment and forming the hyperbranched polyglycerol coating by contacting the activated substrate with the glycidol monomers to initiate polymerisation of the monomers.

In certain embodiments, the method comprises forming a coating with a thickness of 5 nm or more, 6 nm or more, 7 nm or more, 8 nm or more, 9 nm or more, 10 nm or more, 20 nm or more, 50 nm or more or 100 nm or more.

In certain embodiments, the method comprises forming a coating with a thickness of at least 5 nm, at least 6 nm, at least 7 nm, at least 8 nm, at least 9 nm, at least 10 nm, at least 20 nm, at least 50 nm or at least 100 nm. A suitable thickness relevant to the application of the device may be selected. Methods for determining the thickness of a coating are known in the art.

In certain embodiments, the coating of the polymeric substrate results in the substrate having one or more characteristics in use selected from reduced attachment of platelets to the coated substrate, reduced attachment of cells and/or proteins to the coated substrate, reduced fouling, reduced clotting, reduced thrombosis and reduced anastomotic hyperplasia.

In certain embodiments, the reduction of one or more of the aforementioned characteristics comprises a reduction by at least 10%, at least 20%, at least 30%, at least 40%, at least 50%, at least 60%, at least 70%, at least 80%, or at least 90%, as compared to an uncoated substrate.

In certain embodiments, the attachment of platelets and/or the attachment of cells is reduced by at least 10%, at least 20%, at least 30%, at least 40%, at least 50%, at least 60%, at least 70%, at least 80%, or at least 90%, as compared to an uncoated substrate.

Certain embodiments of the present disclosure provide a hyperbranched polyglycerol coated polymeric substrate produced by a method as described herein.

Certain embodiments of the present disclosure provide a medical device comprising a coated polymeric substrate as described herein.

Certain embodiments of the present disclosure provide a polymeric substrate comprising a surface coated with a hyperbranched polyglycerol produced by a method as described herein.

Certain embodiments of the present disclosure provide a method of coating a polymeric surface with a hyperbranched polyglycerol, the method comprising polymerisation of glycidol monomers to form a hyperbranched polyglycerol on the polymeric surface and thereby coating the polymeric surface with the hyperbranched polyglycerol.

Certain embodiments of the present disclosure provide a method of producing a medical device with one or more of reduced platelet attachment, reduced fouling, reduced cell attachment, reduced inflammatory cell attachment, reduced anastomotic hyperplasia, reduced clotting and/or reduced thrombosis, the method comprising using a hyperbranched polyglycerol coated polymeric material in the device to reduce platelet attachment, fouling, cell attachment, inflammatory cell attachment, anastomotic hyperplasia, clotting and/or thrombosis associated with the medical device.

Certain embodiments of the present disclosure provide a method of producing a polymeric medical device with one or more of reduced platelet attachment, reduced fouling, reduced cell attachment, reduced inflammatory cell attachment, reduced anastomotic hyperplasia, reduced clotting and/or reduced thrombosis, the method comprising coating polymeric material in the medical device with a hyperbranched polyglycerol.

Certain embodiments of the present disclosure provide a medical device produced by a method as described herein.

Methods for assessing platelet and cell attachment to materials are known in the art. For example, cells may be stained with specific cell stains/markers and these used to identify cells associated with a material. Methods for assessing fouling are known in the art, and include for example, visualisation of the material for attached matter (eg proteins, cells, platelets) by light microscopy. Methods for assessing anastomotic hyperplasia are known in the art, and include for example, histologic assessment of implanted materials or assessment of hyperplasia in animal models using flow analysis. Methods for assessing clotting or thrombosis are known in the art, and include for example, assessment of implanted materials for the presence of a clot/thrombus and/or in vitro studies as described herein.

The present disclosure is further described by the following examples. It is to be understood that the following description is for the purpose of describing particular embodiments only and is not intended to be limiting with respect to the above description.

Example 1

Grafting of Polytetrafluoroethylene Polymer

Methodology

Glycidol (Sigma, 96%) was distilled at 60° C. under vacuum and stored in sealed 1.5 mL eppendorf tubes at −2.0° C. until required.

ePTFE substrates (GORE-TEX® Vascular Graft) were cut into 1 cm×1 cm squares and sonicated in dichloromethane (DCM) for 10 minutes and then a further 5 minutes in fresh DCM to remove organic contaminants.

The clean substrates were dried under a stream of nitrogen gas and placed at the centre of the vacuum chamber of a plasma cleaner fitted with an argon gas line-in. Substrates were either placed directly on a quartz crystal shelf or suspended from a stainless steel wire frame purpose built for positioning tubular devices at the centre of the chamber. The vacuum chamber was pumped down to a pressure ≤$2.0×10^{-2}$ mbar with intermittent purging with pure argon to ensure minimal atmospheric contamination in the chamber.

Upon reaching the desired pressure, $2.0×10^{-2}$ mbar, radio frequency (RF) induced plasma was ignited at maximum power (18 W RF output) for 20 minutes.

Following plasma treatment the chamber was backfilled with pure argon and the samples transferred directly into distilled glycidol. The samples were then incubated at 100° C. for up to 24 hours.

Following incubation the unreacted glycidol was removed and samples washed ×3 with 100% ethanol and then soaked in 100% ethanol for at least 24 hours.

The process described above resulted in coating of ePTFE with a hyperbranched polyglycerol. The substrate was activated through a radio frequency (RF) induced plasma process free of organic solvents. Immediate immersion of the activated substrates in neat (solvent free) glycidol initiated ring-opening polymerisation of the monomer directly from the surface.

The process of grafting hyperbranched polyglycerol (HPG) onto polymeric surfaces provides a green chemistry process that can be readily implemented on an industrial scale and inserted into existing production lines for processing relevant medical devices.

Example 2

Grafting of Hyperbranched Polyglycerol onto ePTFE Results in a Coating that has Reduced Fouling and Reduced Platelet Adhesion Methodology Platelet rich plasma (PRP) was isolated from human whole blood donated by a healthy non-smoker adult. Whole blood was collected into 4×BD Vacutainers containing 1 mL of ACD (Acid citrate dextrose) solution B then transferred into plastic centrifuge tubes. The whole blood was spun at 250 g for 15 minutes with no brake. PRP was taken from the top portion of the supernatant (platelet count=193 million cells/mL, white blood cells=1.32 million cells/mL).

HPG-grafted ePTFE, along with the controls, were washed ×3 with sterile PBS (pH 7.4) then incubated in freshly isolated PRP for 2 hours at 37° C. and 5% $CO_2$.

Following incubation, surfaces were washed lightly ×3 with warm PBS and fixed with paraformaldehyde solution (4% in PBS) for 20 minutes. Fixed materials were washed ×3 with PBS and stained with CFSE (Carboxyfluorescein succinimidyl ester) and DAPI (4',6-diamidino-2-phenylindole) (1:2000 in PBS pH 7.4) for 20 minutes at 37° C., then washed ×3 with PBS and ×3 with deionised water.

Substrates were imaged on a Zeiss 710 confocal microscope.

Results

The results are shown in FIG. 1. Panel A shows the results of incubating bare ePTFE (GORE-TEX®) in platelet rich plasma. Panel B shows the results of incubating the HPG coated ePTFE (GORE-TEX®) in platelet rich plasma.

Platelets could clearly be observed to attach in high numbers to the bare substrate while the HPG-grafted SS remained almost completely platelet free. These studies indicated that the MPG modified GORE-TEA® had a greatly reduced platelet attachment.

Example 3

Water Contact Angle Measurements on HPG-Coated ePFTE

Methodology ePFTE samples (bare and modified) were fastened to a glass microscope slide using double sided tape to ensure the samples remained flat. Milli-Q water (18.2 MΩcm, 3 μL) was placed onto the samples using a 100 μL Hamilton syringe fitted with a hydrophobic sleeve, and images were captured using a Panasonic WV-BP550/G CCTV camera. The static contact angle was measured using ImageJ software with the drop analysis plugin. All measurements were repeated a minimum of three times, and the results were averaged.

Results

Figure 2:
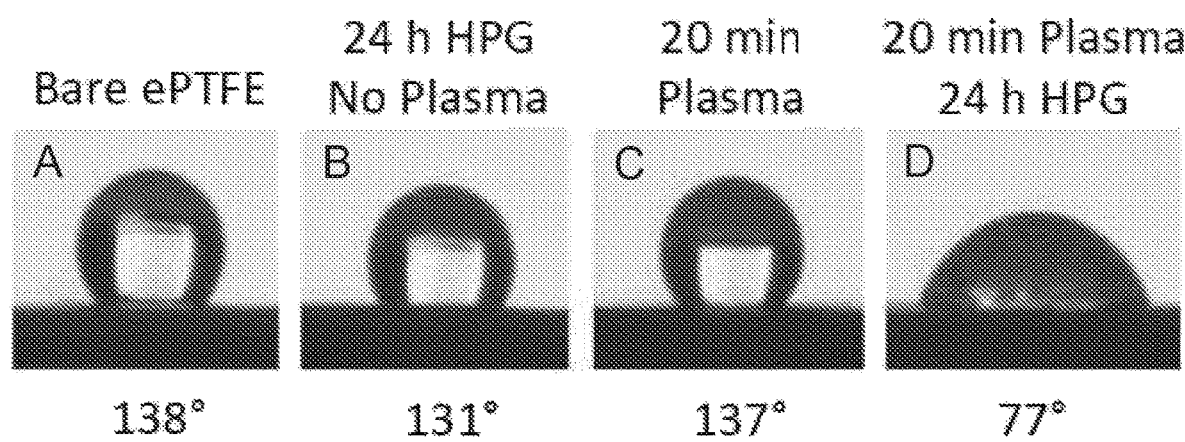
FIG. 2 shows the static water contact angles for ePTFE graft materials throughout stages of the HPG-grafting procedure. A) bare ePTFE; B) bare ePTFE incubated in glycidol monomer for 24 hours at 100° C. without plasma activation; C) ePFTE treated with argon plasma for 20 minutes but not incubated in glycidol monomer; and D) ePTFE treated with argon plasma for 20 minutes followed immediately by incubation in glycidol monomer for 24 hours at 100° C.

The results are provided in FIG. 2, which shows the static water contact angles for ePFTE graft materials throughout stages of the HPG-grafting procedure. A) bare ePTFE; B)

bare ePTFE incubated in glycidol monomer for 24 hours at 100° C. without plasma activation; C) ePFTE treated with argon plasma for 20 minutes but not incubated in glycidol monomer; and ePTFE treated with argon plasma for 20 minutes followed immediately by incubation in glycidol monomer for 24 hours at 100° C.

The contact angle for bare ePTFE indicated the highly hydrophobic nature of the material and was within the expected range. Bare ePTFE incubated in glycidol displayed a slight decrease in contact angle and therefore increased hydrophilicity. This was accounted for by the adsorption of small quantities of glycidol monomer and/or self-initiated HPG formed in solution. Argon plasma treatment of the ePTFE did not result in a change in contact angle from the untreated bare ePTFE and therefore it was considered that elemental substitution at the molecular level (i.e. replacement of fluorine with argon, oxygen, nitrogen etc.) resulting in a change in chemical environment had not occurred during this treatment. The combination of argon plasma activation and incubation in glycidol monomer resulted in a large increase in hydrophilicity of the ePTFE material. This was considered to be the result of the formation of HPG directly from the carbon backbone of PTFE presented at the surface of the material.

Conclusions

This data indicates that HPG-grafting is not initiated from bare ePTFE without plasma activation while plasma activation alone does not change the hydrophilicity of the bare substrate. However, combining plasma activation and HPG-grafting modifies the surface and increases hydrophilicity.

Example 4

Manufacture of HPG Coated Vascular Grafts

Vascular grafts may be manufactured by a method known in the art, from a material such as PTFE. HPG coating of the polymeric vascular graft may be undertaken as described herein.

Initially, the graft may optionally be subject to some form of cleaning in readiness for plasma treatment, although it is anticipated in most circumstances that a graft may be suitable for plasma treatment without such cleaning.

The clean graft may then be placed at the centre of a vacuum chamber of a plasma cleaner fitted with an argon gas line-in. The vacuum chamber is pumped down to a pressure $<2.0\times10^{-2}$ mbar with intermittent purging with pure argon to ensure minimal atmospheric contamination in the chamber. Upon reaching the desired pressure, radio frequency (RF) induced plasma may be used at maximum power (18 W RF output) for 20 minutes.

Following plasma treatment the chamber may then be backfilled with pure argon and the graft transferred directly into distilled glycidol and then incubated at 100° C. for up to 24 hours to coat with HPG.

Following incubation, the graft may be washed in suitable solvent (such as water and/or ethanol), dried and sterilised, and stored in suitable packaging ready for use.

Example 5

Use of a HPG Coated Vascular Graft

Typically a HPG coated vascular graft will be supplied sterile in packaging.

The HPG coated grafts may be used, for example, as vascular prostheses for replacement or bypass of diseased vessels in patients suffering occlusive or aneurysmal diseases, in trauma patients requiring vascular replacement, for dialysis access, or for other vascular procedures.

Operative techniques for using vascular grafts are known in the art, and may be practiced by a suitably qualified medical practitioner.

Example 6

Grafting of a Polyurethane Polymer with HPG

A suitable methodology to coat polyurethane with HPG is as follows:

Glycidol (available from Sigma, 96%; Catalogue No. G5809) may be distilled at 60° C. under vacuum and stored in sealed 1.5 mL eppendorf tubes at −20° C. until required.

Polyurethane substrates may be cut into a suitable size. Substrates may be washed with ethanol or methanol to remove contaminants.

The clean substrate may then be dried under a stream of nitrogen gas and placed at the centre of the vacuum chamber of a plasma cleaner fitted with an argon or oxygen gas line-in. Substrates may then be placed directly on an aluminium shelf or suspended from an aluminium sample jig for positioning towards the centre of the chamber. The vacuum chamber may be pumped down to a pressure $<2.0\times10^{-2}$ mbar with intermittent purging with pure argon or oxygen to ensure minimal atmospheric contamination in the chamber.

Upon reaching the desired pressure, $2.0\times10^{-2}$ mbar, radio frequency (RF) induced plasma may then be employed at a power sufficient to maintain a low pressure plasma (18 W RF output) for 20 minutes, although other power levels and treatment times may be selected.

Following plasma treatment, the chamber may be backfilled with pure argon or oxygen and the samples then transferred directly into distilled glycidol. The samples may then be incubated at temperatures between 70 and 100° C. for a suitable time, for example up to 24 hours. This will result in the coating of the polyurethane substrate with hyperbranched polyglycerol.

Following incubation, unreacted glycidol may be removed and the samples washed with 100% ethanol or 100% methanol or water and then subsequently soaked in 100% ethanol or 100% methanol or water.

The process described above may be used to coat polyurethane with a hyperbranched polyglycerol. Analysis of the coating may be undertaken by X-ray photoelectron spectroscopy analysis (to analyse chemical composition and film thickness below 10 nm) and water contact angle measurements (to assess hydrophilicity).

Manufacture of medical devices using HPG coated polyurethane may be undertaken in a similar fashion as that described in Example 4.

Although the present disclosure has been described with reference to particular embodiments, it will be appreciated that the disclosure may be embodied in many other forms. It will also be appreciated that the disclosure described herein is susceptible to variations and modifications other than those specifically described. It is to be understood that the disclosure includes all such variations and modifications. The disclosure also includes all of the steps, features, compositions and compounds referred to, or indicated in this specification, individually or collectively, and any and all combinations of any two or more of the steps or features.

Also, it is to be noted that, as used herein, the singular forms "a", "an" and "the" include plural aspects unless the context already dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Reference to any prior art in this specification is not, and should not be taken as, an acknowledgment or any form of suggestion that this prior art forms part of the common general knowledge in any country.

The subject headings used herein are included only for the ease of reference of the reader and should not be used to limit the subject matter found throughout the disclosure or the claims. The subject headings should not be used in construing the scope of the claims or the claim limitations.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

The invention claimed is:

1. A method of coating a polymeric substrate with a hyperbranched polyglycerol, the method comprising polymerisation of glycidol monomers to form a hyperbranched polyglycerol on the polymeric substrate activated by plasma treatment and thereby coating the polymeric substrate with the hyperbranched polyglycerol.

2. A polymeric substrate coated by the method according to claim 1.

3. A medical device comprising a coated polymeric substrate according to claim 2.

* * * * *